US008278101B2

(12) United States Patent
Navran, Jr.

(10) Patent No.: US 8,278,101 B2
(45) Date of Patent: Oct. 2, 2012

(54) STEM CELL BIOPROCESSING AND CELL EXPANSION

(75) Inventor: Stephen S. Navran, Jr., Houston, TX (US)

(73) Assignee: Synthecon, Inc., Houston, TX (US)

( * ) Notice: Subject to any disclaimer, the term of this patent is extended or adjusted under 35 U.S.C. 154(b) by 167 days.

(21) Appl. No.: 12/928,116

(22) Filed: Dec. 3, 2010

(65) Prior Publication Data

US 2011/0136226 A1 Jun. 9, 2011

Related U.S. Application Data

(60) Provisional application No. 61/283,705, filed on Dec. 7, 2009.

(51) Int. Cl.
*C12N 5/07* (2010.01)
*C12N 5/077* (2010.01)
*C12N 5/078* (2010.01)
*C12N 5/0789* (2010.01)
*C12M 3/00* (2006.01)

(52) U.S. Cl. ............. 435/373; 435/289.1; 435/347; 435/383; 435/297.1

(58) Field of Classification Search .................. None
See application file for complete search history.

(56) References Cited

U.S. PATENT DOCUMENTS

| | | | |
|---|---|---|---|
| 5,763,279 A * | 6/1998 | Schwarz et al. | 435/383 |
| 6,306,644 B1 * | 10/2001 | Marx et al. | 435/294.1 |
| 6,607,910 B1 * | 8/2003 | Dimitrijevich et al. | 435/297.1 |
| 6,841,384 B2 * | 1/2005 | Robbins, Jr. | 435/325 |
| 6,911,201 B1 * | 6/2005 | Merchav et al. | 424/93.7 |
| 7,144,727 B2 * | 12/2006 | Akers et al. | 435/294.1 |
| 7,270,996 B2 * | 9/2007 | Cannon et al. | 435/293.1 |
| 7,390,653 B2 * | 6/2008 | Akers et al. | 435/297.2 |
| 7,507,581 B2 * | 3/2009 | Navran, Jr. | 435/391 |
| 7,534,609 B2 * | 5/2009 | Merchav et al. | 435/395 |
| 7,678,573 B2 * | 3/2010 | Merchav et al. | 435/404 |
| 7,947,499 B2 * | 5/2011 | Gerecht-Nir et al. | 435/394 |
| 8,076,136 B2 * | 12/2011 | Clarke et al. | 435/373 |
| 8,080,417 B2 * | 12/2011 | Peled et al. | 435/373 |
| 2002/0090725 A1 * | 7/2002 | Simpson et al. | 435/402 |
| 2003/0129742 A1 * | 7/2003 | Helmstetter et al. | 435/289.1 |
| 2006/0205071 A1 * | 9/2006 | Hasson et al. | 435/366 |
| 2007/0111310 A1 * | 5/2007 | Cohen et al. | 435/366 |
| 2008/0118477 A1 * | 5/2008 | Christopherson | 424/93.7 |
| 2008/0166328 A1 * | 7/2008 | Harmon et al. | 424/93.7 |
| 2008/0299649 A1 * | 12/2008 | Martin et al. | 435/297.1 |
| 2009/0111180 A1 * | 4/2009 | Vilendrer et al. | 435/395 |
| 2010/0034793 A1 * | 2/2010 | McNiece et al. | 424/93.71 |
| 2010/0167398 A1 * | 7/2010 | Sasai et al. | 435/366 |
| 2010/0233130 A1 * | 9/2010 | Meretzki | 424/93.7 |
| 2011/0091926 A1 * | 4/2011 | Frerich | 435/29 |
| 2011/0136226 A1 * | 6/2011 | Navran, Jr. | 435/347 |
| 2011/0263013 A1 * | 10/2011 | Shamblott et al. | 435/347 |
| 2012/0083029 A1 * | 4/2012 | Tsumura et al. | 435/289.1 |
| 2012/0129207 A1 * | 5/2012 | Yarmush et al. | 435/29 |

* cited by examiner

*Primary Examiner* — Daniel C Gamett
(74) *Attorney, Agent, or Firm* — Elizabeth R. Hall (57) ABSTRACT

A stem cell niche for expanding stem cells in culture is described. The stem cell niche includes a scaffold, a plurality of stromal mesenchymal stem cells, and a plurality of umbilical cord blood stem cells grown in a rotating culture chamber. One embodiment of the rotating culture chamber has a fluid-filled compartment in which the umbilical cord blood stem cells are grown in the presence of the mesenchymal stem cells seeded on the scaffold. The culture chamber has a dual flow valving member at each end, wherein a first flow path passes under a molecular cut-off membrane covering a central core that transverses the culture chamber and a second flow path flows through the culture chamber and allows cells to be harvested while in suspension.

1 Claim, 9 Drawing Sheets

STEM CELL BIOPROCESSING AND CELL EXPANSION

CROSS REFERENCE TO RELATED APPLICATIONS

This application claims priority to pending U.S. Patent Application Ser. No. 61/283,705 filed Dec. 7, 2009 by inventor Stephen S. Navran, Jr. entitled "Stem Cell Bioprocessing and Cell Expansion." The entire text of the above-referenced disclosures is incorporated by reference herein.

STATEMENT AS TO FEDERALLY SPONSORED RESEARCH

This invention was made with government support under SBIR Grant Number 2R44HD058391-02 awarded by NIH. The government has certain rights in the invention.

BACKGROUND OF THE INVENTION

1. Field of the Invention

The present invention relates to a method and an apparatus for culturing stem cells. More particularly, the present invention relates to a culture chamber having a dual flow valving member, wherein a first flow path passes under a molecular cut-off membrane covering a central core that transverses the culture chamber and a second flow path flows through the culture chamber and allows cells to be harvested while in suspension.

2. Description of the Related Art

The use of stem cells for regenerative therapies is one of the most exciting prospects in biomedical research. The translation of laboratory findings in stem cell biology into clinical therapies must overcome significant bioprocessing and safety challenges.

Stem cells are a particularly attractive source of material for regenerative medicine by virtue of their extensive ability to proliferate and differentiate into multiple cell lineages. However, this characteristic is associated with a risk of malignant transformation. If regenerative therapies using stem cells are to be realized on a practical scale, bioprocessing technologies must be developed which can achieve the necessary cell expansion while minimizing the risks of tumor development.

Current approaches to this problem have relied on conventional cell culture technologies which have proven adequate for cell-derived products such as antibodies and recombinant proteins but less than optimal for stem cells.

SUMMARY OF THE INVENTION

Embodiments of the invention contemplate the creation of a stem cell niche having a scaffold, a plurality of stromal mesenchymal stem cells, and a plurality of umbilical cord blood stem cells all grown in a rotating culture chamber.

One embodiment of the culture chamber has a fluid-filled compartment in which stem cells are cultured. The culture chamber has a dual flow valving member at each end, wherein a first flow path passes under a molecular cut-off membrane covering a central core that transverses the culture chamber and a second flow path flows through the culture chamber and allows cells to be harvested while in suspension.

The foregoing has outlined rather broadly several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed might be readily utilized as a basis for modifying or redesigning the structures for carrying out the same purposes as the invention. It should be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

Embodiments of the invention include a stem cell niche for expanding stem cells in culture. The stem cell niche includes a scaffold, a plurality of stromal mesenchymal stem cells (MSC) seeded and grown on the scaffold, and a plurality of umbilical cord blood (UCB) stem cells grown in a rotating culture chamber in the presence of the mesenchymal stem cells grown on the scaffold. One embodiment of the rotating culture chamber has a fluid-filled compartment in which the umbilical cord blood stem cells are grown in the presence of the mesenchymal stem cells seeded on the scaffold. The culture chamber has a dual flow valving member at each end, wherein a first flow path passes under a molecular cut-off membrane covering a central core that transverses the culture chamber and a second flow path flows directly through the culture chamber.

Incoming nutrients and/or biological modifiers are transported through the membrane of the first fluid path into the culture compartment and metabolic waste products are transported away from the fluid-filled culture compartment through the membrane and out the chamber outlet. The second fluid path allows the expanded stem cells to be harvested while in suspension.

The potential for the used of stem cells for regenerative medicine has produced considerable excitement in the scientific community. Laboratory studies have shown that it may be possible to produce functional replacements for diseased or injured tissues. However, the future of stem cells in regenerative medicine require that methods are developed that allow investigators to expand a small number of stem cells to a much larger number of stem cells as to be of practical use in creating tissues for regenerative medicine.

Problems with the self renewal of stem cells in culture are apparently related to the fact that the conventional cell culture environment does not resemble the in vivo environment in which the stem cells normally exist. In vivo, stem cells are maintained in a largely quiescent state. Most cell divisions lead to the production of a stem cell and a daughter cell which will continue to divide to eventually produce a tissue. The numbers of stem cells actually change very little. This situation is thought to have evolved to minimize the possibility of mutations which could lead to uncontrolled growth or cancer.

The Stem Cell Niche

Embodiments of the stem cell niche described herein include a scaffold, a plurality of stromal mesenchymal stem cells (MSC) seeded and grown on the scaffold, and a plurality of umbilical cord blood (UCB) stem cells grown in a rotating culture chamber in the presence of the mesenchymal stem cells grown on the scaffold. The NASA-designed Rotary Cell Culture System (RCCS) is ideal for mimicking the normal in vivo environment of stem cells in the bone marrow. By co-culturing MSC supporting cells with UCB stem cells on a polymer scaffolding material, a culture system which mimics an in vivo stem cell niche will allow the long term maintenance of stem cells and enable the continuous harvesting of cells in a controlled manner.

In addressing the problems associated with stem cell expansion, the role of the microenvironment or stem cell niche has become evident (Scadden, D. T. "The stem cell niche as an entity of action", Nature 441: 1075-1079, 2006). The stromal or mesenchymal stem cells (MSC) first discovered in the bone marrow provide a rich environment of soluble factors, extracellular matrix and adhesion molecules that regulate the balance between self renewal and differentiation of stem cells (Yamashita, Y. M., et al. "Signaling in stem cell niches: lessons from the *Drosophilia* germline", J. Cell Sci. 118: 665-672, 2005).

Because stem cells are normally maintained within the niche in a quiescent state, it is not surprising that attempts to massively expand them for therapeutic applications in conventional culture systems have met with little success. As many investigators have pointed out, the existence of a population of cells with unlimited growth potential, requires stringent control of proliferation to prevent the emergence of cancerous cells, a function which has been proposed for the stem cell niche (Li, L. and Neaves, W. B. "Normal stem cells and cancer stem cells: the niche matters", Cancer Res. 66: 4553-4557, 2006; Chepko, G., et al. "Differential alteration of stem and other cell populations in ducts and lobules of TGFα and c-Myc transgenic mouse mammary epithelium", Tissue Cell 37: 393-412, 2005).

Recent attempts to expand umbilical cord blood (UCB) for bone marrow transplants have highlighted some of the problems in the practical use of stem cells for regenerative medicine. Umbilical cord blood is an attractive alternative to bone marrow transplantation because it contains hematopoietic stem cells (HSC) with relatively high immunologic tolerance and greater potential for proliferation than adult bone marrow (Wagner, J. E., et al. "Transplantation of unrelated donor umbilical cord blood in 102 patients with malignant and nonmalignant diseases: influence of CD34 cell dose and HLA disparity on treatment-related mortality and survival", Blood 100: 1611-1618, 2002).

Yet the limited number of stem cells in an average UCB unit has delayed engraftment as compared to using the more numerous bone marrow or mobilized peripheral blood cells. Thus, UCB stem cell engraftment has mostly been restricted to pediatric patients requiring fewer cells. To date all attempts to expand UCB stem cells ex vivo using hematopoietic growth factors have failed to improve engraftment (Jarosak, J., et al. "Augmentation of umbilical cord blood (UCB) transplantation with ex-vivo-expanded UCB cells: results of a phase 1 trial using the AastromReplicell system", Blood 101: 5061-5057, 2003; Devine, S. M., et al. "Clinical application of hematopoietic progenitor cell expansion: current status and future prospects", Bone Marrow Transplant 31:241-252, 2003). In animal studies cytokine supplementation has produced little or no increase in long-term repopulating stem cells Although the use of UCB cells for the treatment of non-hematological diseases is beginning to attract considerable interest because of their multilineage potential (McGuckin, C. P., et al. "Production of stem cells with embryonic characteristics from human umbilical cord blood", Cell Prol. 38:245-255, 2005; Yoshida, S., et al. "Human cord blood-derived cells generate insulin-producing cells in vivio", Stem Cells 23:1409-1416, 2005; McGuckin, C., et al. "Embryonic-like stem cells from umbilical cord blood and potential for neural modeling", Acta Neurobiol. Exp. 66:321-329, 2006), the limited numbers of cells available and the difficulty of expanding the stem cell population impacts every practical application of UCB stem cells for regenerative medicine.

Embodiments of the invention include the development of an artificial stem cell niche to address the current inability to maintain stem cells in an undifferentiated state during expansion stimulated by mixtures of exogenous growth factors (i.e., the production of long-term repopulating cells, LTRC) and to limit the risk of genetic instability leading to cell transformation.

One embodiment of an artificial stem cell niche co-cultures bone marrow stromal cells, with UCBs or bone marrow-derived HSCs on three dimensional scaffolding in a perfused NASA-designed Rotary Cell Culture System (RCCS).

The Rotary Cell Culture System with a Dual Flow Valving Member

The RCCS is a horizontally rotating, zero head space clinostat with a cylindrical culture chamber that simulates the effects of microgravity by maintaining cells in suspension at very low shear stress (0.8 dynes/cm2) with high diffusion rates of oxygen, nutrients and waste. The culture vessel is completely filled with media avoiding a headspace which can create cell-damaging bubbles and turbulence as with roller bottles or stirred culture vessels. Shear stress has long been known to have adverse effects on cultured cells.

Figure 1:
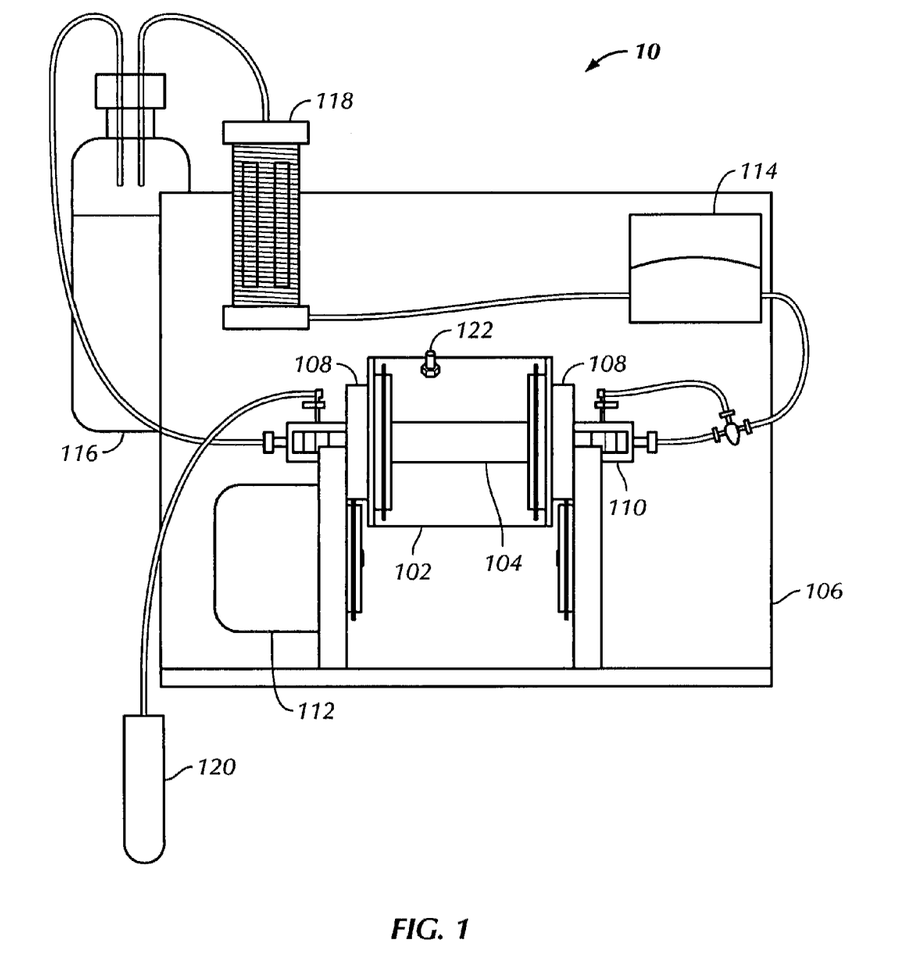
FIG. 1 shows a schematic view of one embodiment of the rotary cell culture chamber having a center core surrounded by a molecular weight cut-off membrane and a dual flow valving member

One embodiment of the perfused version of the RCCS 10 is schematically illustrated in FIG. 1. The RCCS has a rotating cylindrical vessel 102 with a perfusion core covered with a molecular weight cut-off membrane 104 that transverses the vessel 102. Each end of the rotating vessel 102 has an end cap 108 and a dual flow coupling 110. The vessel 102 sits on a rotator base 106 and is rotated by a motor 112. The media is pumped from an external reservoir 116 through a gas exchanger 118 by a peristaltic pump 114. The vessel 102 has a sample port 122 through which samples can be injected or removed from vessel 102 when rotation of the vessel 102 is stopped.

Figure 2:
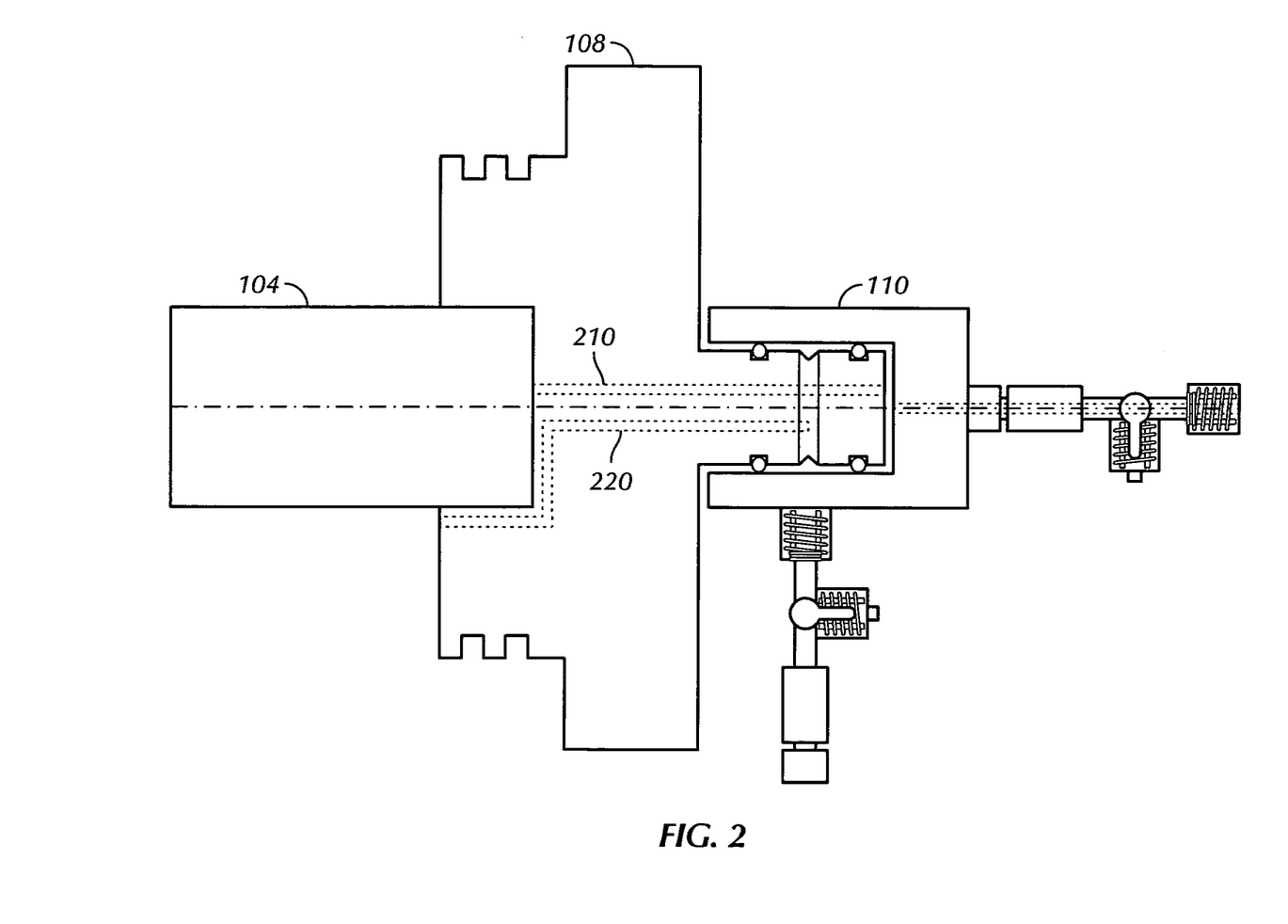
FIG. 2 shows a longitudinal cross-sectional view of the dual flow valving member.
Figure 4:
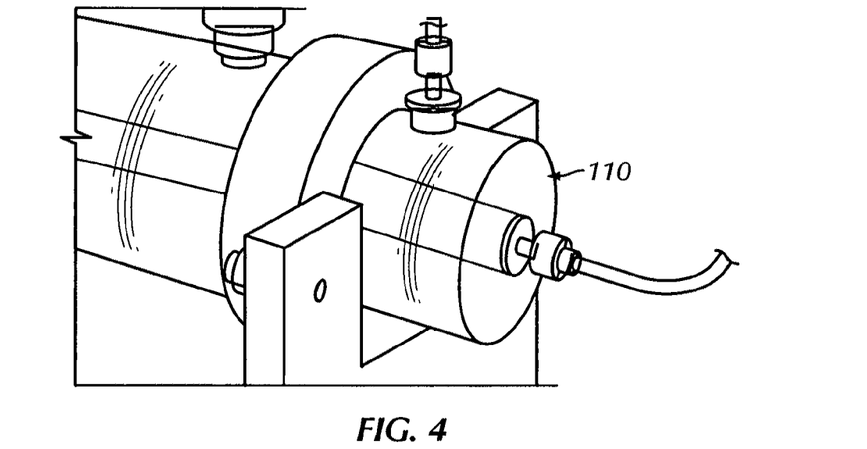
FIG. 4 is a photograph of the dual flow valving member.

The dual flow coupling or valving member 110 shown in FIGS. 2 and 4 has two selectably operable channels, where each channel provides a rotating fluid path. The first channel provides a first fluid path 210 for the media to pass under the molecular cut-off membrane covering the central perfusion core 104, while the second channel provides a second fluid path 220 that flows directly through the culture chamber.

The first fluid path 210 provides a path for changing the media in the vessel 102 without disturbing the cell culture.

The media is pumped into the vessel through the first channel and into the first fluid path 210 between the central core and the molecular weight cut-off membrane covering the core with no direct flow of media into the cell chamber. Nutrient, waste and gas exchange take place across the membrane. The advantages of this arrangement are that the cells in the bioreactor vessel 102 are not directly exposed to the media flow, avoiding turbulence. The pore sizes of the dialysis membranes range from 5 to 50 kD which will retain factors secreted from the stromal cells within the culture chamber.

The second fluid path 220 passes directly into and out of the culture chamber in the vessel 102. This second fluid path 220 allows the expanded stem cells to be harvested while the vessel 102 is rotating and the cells are in suspension. The harvesting of cells from the rotating bioreactor vessel 102 while it is rotating was tested using the dual flow valving member 110.

The testing of stem cell harvesting from the RCCS bioreactor with the dual flow valving member 110 is described below. One hundred Fibra-Cel scaffold disks were placed in the culture vessel 102 with α-MEM media, the rotation of the vessel 102 was initiated and the vessel 102 was perfused with media through the dialysis membrane pathway 210. Then the rotation of the vessel 102 was temporarily stopped and freshly isolated human UCB monocytes were injected into the culture chamber through the sample port 122. The rotation of the culture chamber was restarted and the flow of media was shunted into the second fluid path 220 directly through the cell chamber and the effluent collected with a fraction collector at 2 minute intervals. The flow rate was 5 ml/min. The fractions were centrifuged and resuspended in 1 ml of PBS and counted in a hemocytomer.

Figure 3:
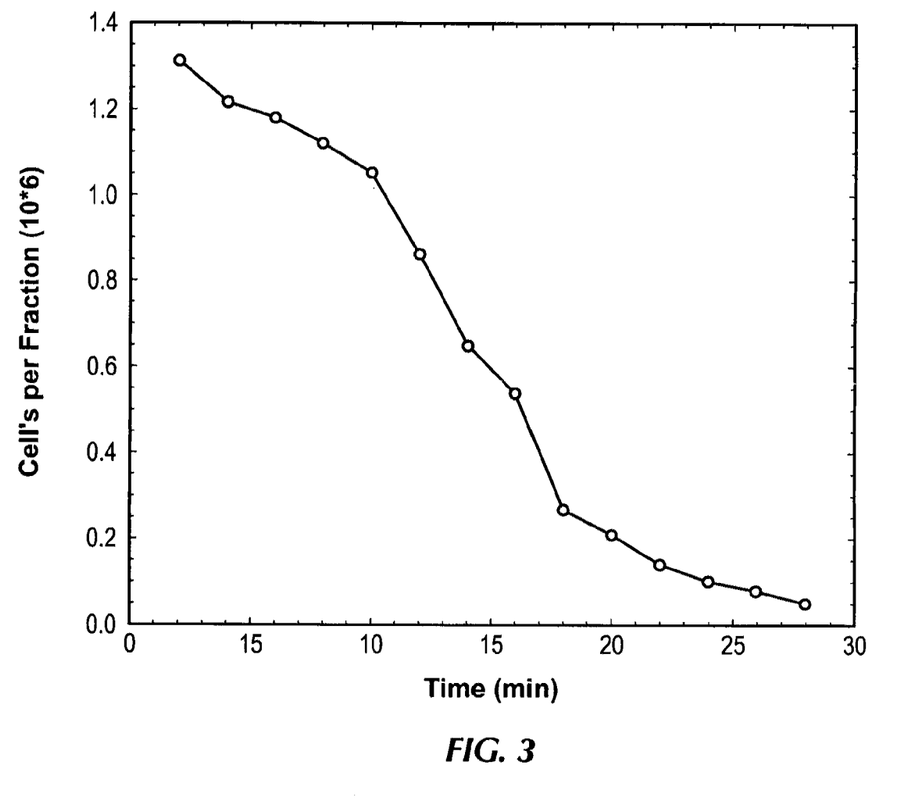
FIG. 3 is a graph of the cells collected from the rotary cell culture chamber when the flow of media was sent through the second fluid path directly through the culture chamber.

The results of this experiment, shown in FIG. 3, demonstrate that the dual valving member 110 RCCS allows the cells to be effectively harvested while in suspension in the RCCS vessel 102. The total number of UCB cells introduced was 9 million and more than 90% of the cells were recovered from the culture chamber using the dual flow valving member 110. As expected the first samples collected contained a significant number of cells and the later samples, collected after media had been added to the culture chamber, contained fewer cells.

Seeding MSCs onto the Scaffolding

Two methods of seeding the MSCs on the Fibra-Cel (New Brunswick Scientific) disks were investigated. The first method used a static seeding of the cells in a multi-well plate. This method has previously been used to seed MSCs in studies co-culturing MSCs with UBC blood cells (Zhang, Y., et al. "Co-culture of Umbilical cord blood CD+ cells with human mesenchymal stem cells", Tissue Eng. 12:2161-2170, 2006). In this procedure, the MSCs were pipetted directly onto the Fibra-Cel disks in a multi-well plate. The cells were allowed to attach for 24 hours and then the disks were transferred to a 10 ml RCCS batch-fed bioreactor and the culture was continued for 7 days. All cultures were done at 32° C. to allow proliferation to proceed. At daily intervals, a disk was removed from the RCCS and the cells growing on the disk were quantitated by measuring the total DNA using the CyQuant Cell Proliferation Assay Kit (Invitrogen).

In the second method, the Fibra-Cel disks were placed in a 10 ml RCCS rotating bioreactor along with suspended MSCs and the cells were allowed to attach dynamically. Disks were assayed for cell growth daily as with the static seeding protocol.

Figure 5:
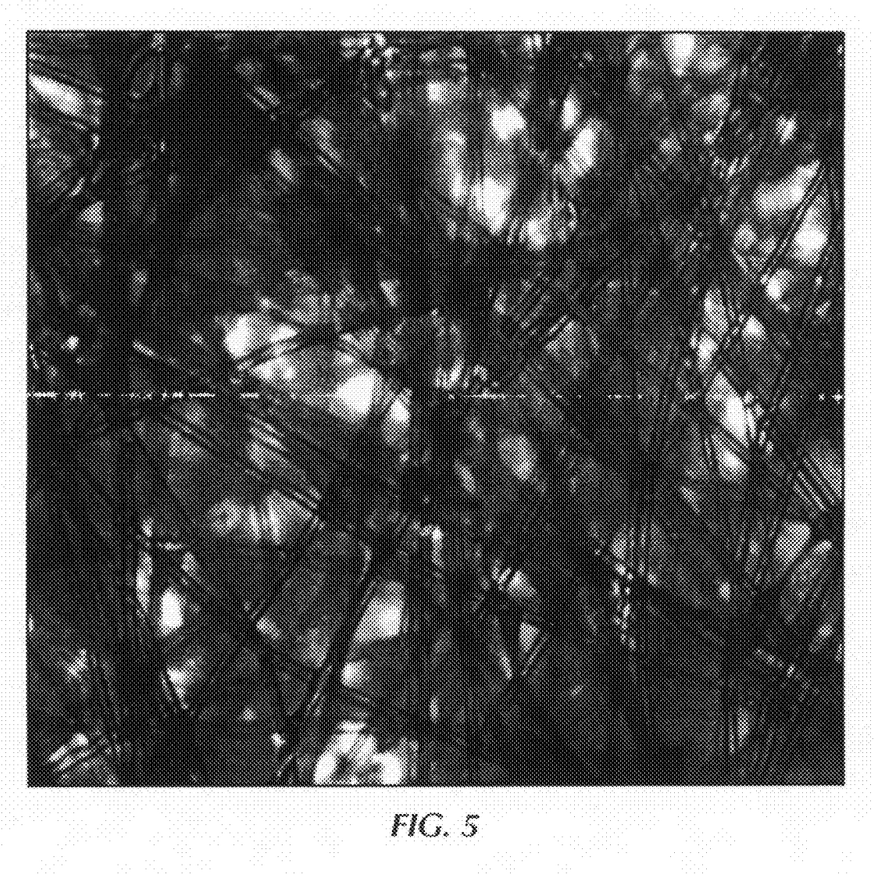
FIG. 5 is a photograph of a Fibra-Cel scaffold without cells growing on the scaffold.
Figure 6:
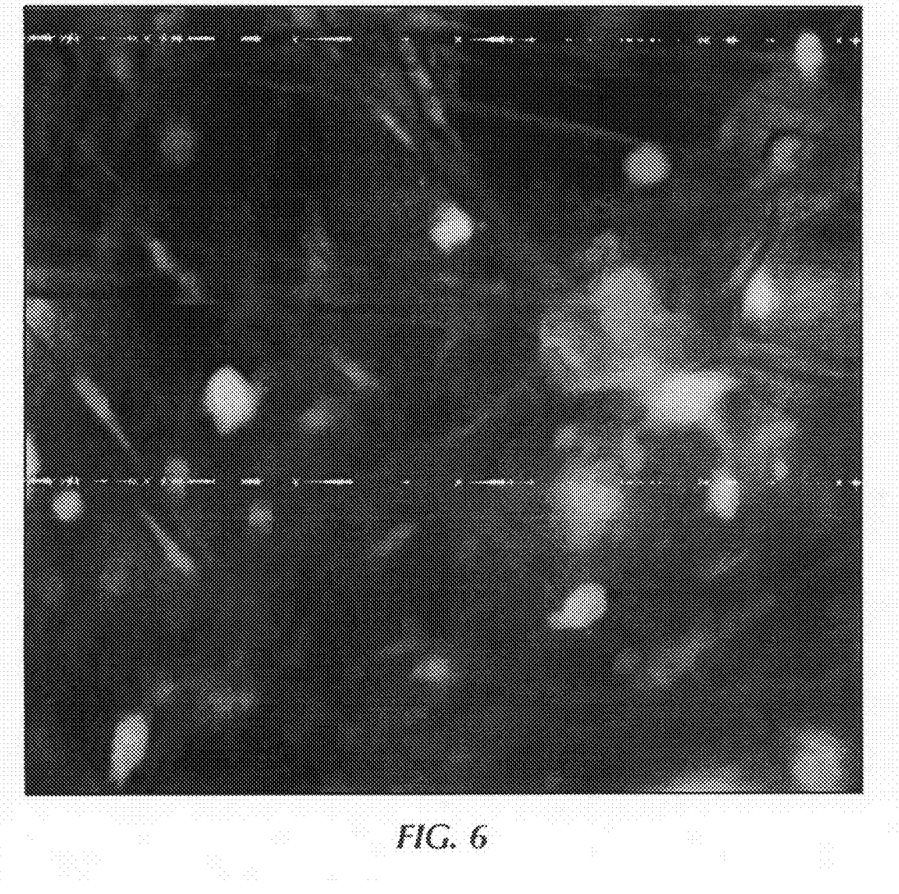
FIG. 6 is a photograph of a Fibra-Cel scaffold with fluorescent MSCs growing on the scaffold.
Figure 7:
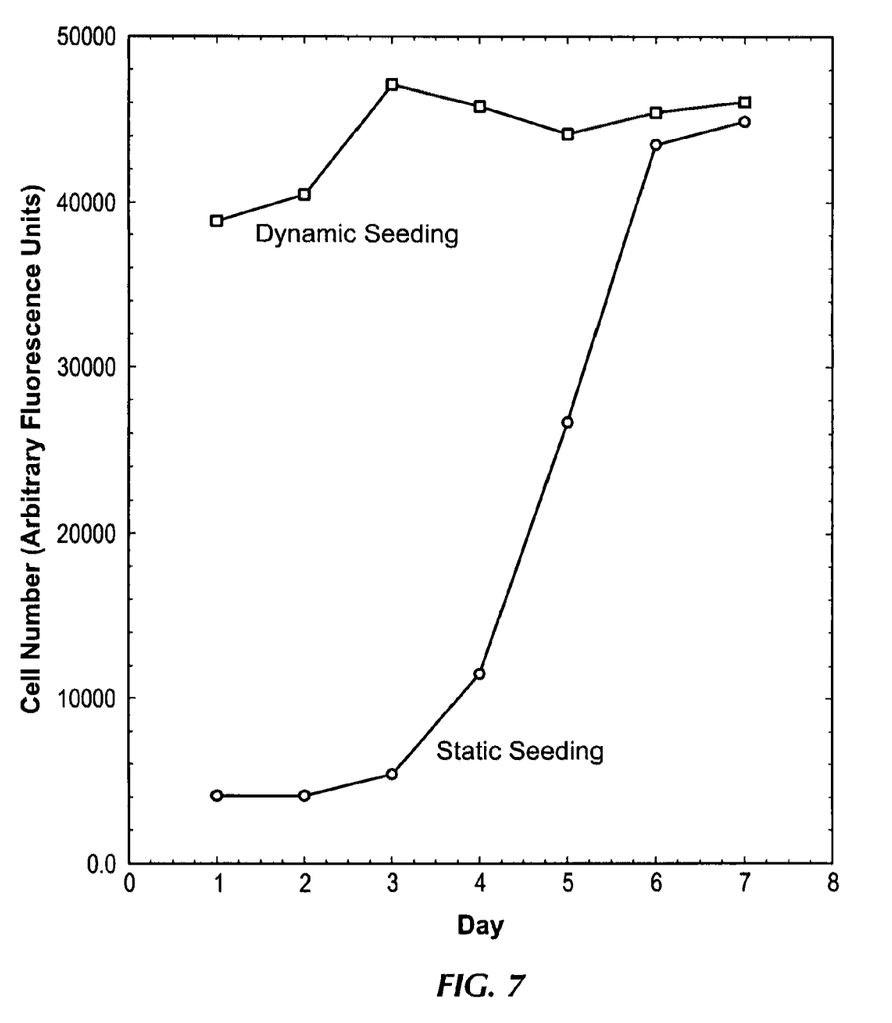
FIG. 7 is a graph comparing the cell number of MSCs on Fibra-Cel scaffolds using a static seeding method and a dynamic seeding method.
Figure 8:
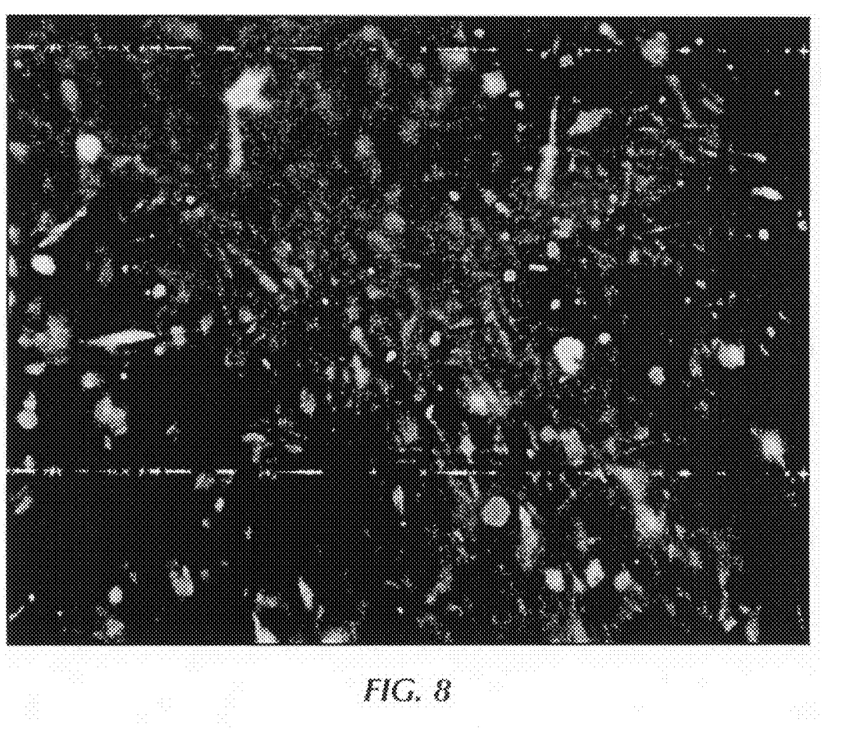
FIG. 8 is a photograph of a co-culture of bone marrow MSC stromal cells expressing GFP (green fluorescence) with UCB cells (red fluorescence) distributed in the scaffold.

FIG. 5 shows the Fibra-Cel scaffold without cells and FIG. 6 shows the Fibra-Cel scaffold with fluorescent MSCs growing on the scaffold. FIG. 7 illustrates the results of the two seeding methods. Using the static method, relatively few MSCs adhered to the scaffold after the first day. Many of the MSCs dropped through the scaffold and attached to the bottom of the multi-well plate. In contrast, the dynamic seeding method allowed many more MSCs to adhere to the scaffold in the first 24 hours. Yet over the 7 day culture period, the statically seeded MSCs reached the same level of confluence as the dynamically seeded cells.

A preferred embodiment of a scaffold used in the artificial niche is manufactured by Biometrix. The scaffold is 5 mm in diameter and 1 mm thick. The Biometrix scaffold has a 3-D macroporous structure that closely resembles the trabecular architecture of the bone marrow. The scaffold material is a cross-linked polycarbonate polyurethane urea generally consisting of 250-500 micrometers of material connected by 100-250 micrometer pores.

Homing of UCB Cells to the MSC-Populated Scaffold

Green Fluorescent Protein (GFP)-expressing MSCs were seeded on Fibra-Cel scaffolds in a 10 ml RCCS bioreactor and allowed to proliferate for 7 days at 32° C. The temperature was then increased to 37° C. to induce quiescence and a UCB mononuclear cell (MNC) fraction was injected through a sample port 122 into the culture chamber. The MNCs were pre-labeled with a fluorescent membrane dye, DiIC18(5)-DS (Molecular Probes), which has an emission peak at 670 nm and does not overlap with the GFP spectra. After 24 hours a scaffold was removed from the vessel and examined by fluorescence microscopy as shown in FIG. 7.

This culture was maintained for over 3 weeks with media changes every 48 hours. Fluorescent labeled UCB cells were continuously observed over that period. If the cells had been dividing, the label would have been diluted and would fade over time. The fact that the label did not fade suggests that the cells were in a quiescent state as would be expected in a niche.

The artificial niche described above was further investigated by using a treatment of HSCs that increases homing and engraftment in vivo. Recently, it has been found that homing and engraftment of cord blood or mobilized peripheral blood HSCs to bone marrow is partly controlled by the expression of CD26 on the surface of HSCs and stromal cells (Kawai, T., et al. "Diprotin A infusion into non obese diabetic/severe combined immunodeficiency mice markedly enhances engraftment of human mobilized CD34+ peripheral blood cells", Stem Cells Dev. 16:361-370, 2007). CD26 is a surface dipeptidylpeptidase which cleaves the aminoterminal dipeptide from stromal derived factor-1 (SDF-1/CXCR12) and other chemokines.

SDF-1 plays an important role in HSC homing and engraftment (Peled, A., et al. "Dependence of human stem cell engraftment and repopulation of NOD/SCID mice on CXCR4", Science 283:845-848, 1999) and its cleavage by CD26 inactivates its chemotactic activity. By inhibiting the CD26 peptidase activity with Diprotin A, a peptide antagonist, it is possible to stimulate homing in vivo. Although both stroma and HSCs express CD26, it has been shown that only a short pretreatment of stem cells alone was necessary to stimulate engraftment in vivo (Campbell, T. B., et al. "Inhibition of CD26 in human cord blood CD34+ cells enhances their engraftment of nonobese diabetic/severe combined immunodeficiency mice", Stem Cells Dev. 16:347-352, 2007; Christopherson II, K. W., et al. "CD26 Inhibition on CD34+ or lineage (−) human umbilical cord blood donor hematopoietic stem cells/hematopoietic progenitor cells improves long-term engraftment into NOD/SCID/Beta2$_{null}$ immunodeficient mice. Stem Cells Dev. 16:355-360, 207).

Whether the homing of UCB cells in an artificial niche could be stimulated by Diprotin A (a tripeptide, Ile-Pro-Ile) was investigated by treating one set of fluorescently labeled UCBs with 5 mM Diprotin A or by treating a control set of fluorescently labeled UCBs with PBS. The cells were treated for 15 minutes at 37° C., washed with media and resuspended.

The Diprotin A treated cells were injected into a first RCCS vessel with MSCs cultured on Fibra-Cel scaffolds and the PBS treated cells were injected into a second RCCS vessel with MSCs cultured on Fibra-Cel scaffolds. After 24 hours, a scaffold was taken from each RCCS vessel and examined by fluorescence microscopy.

Figure 9:
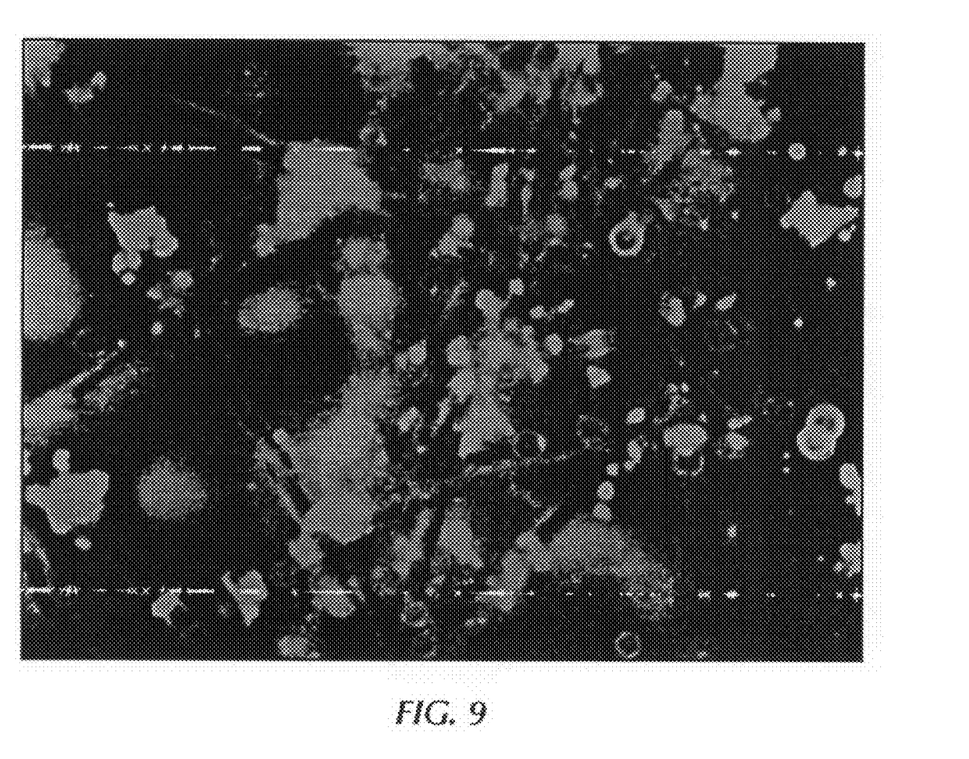
FIG. 9 is a photograph of fluorescent labeled UCB cells that were pretreated with Diprotin A and then cultured for 7 days on a Fibra-Cell scaffold prepopulated with bone marrow MSCs.
Figure 10:
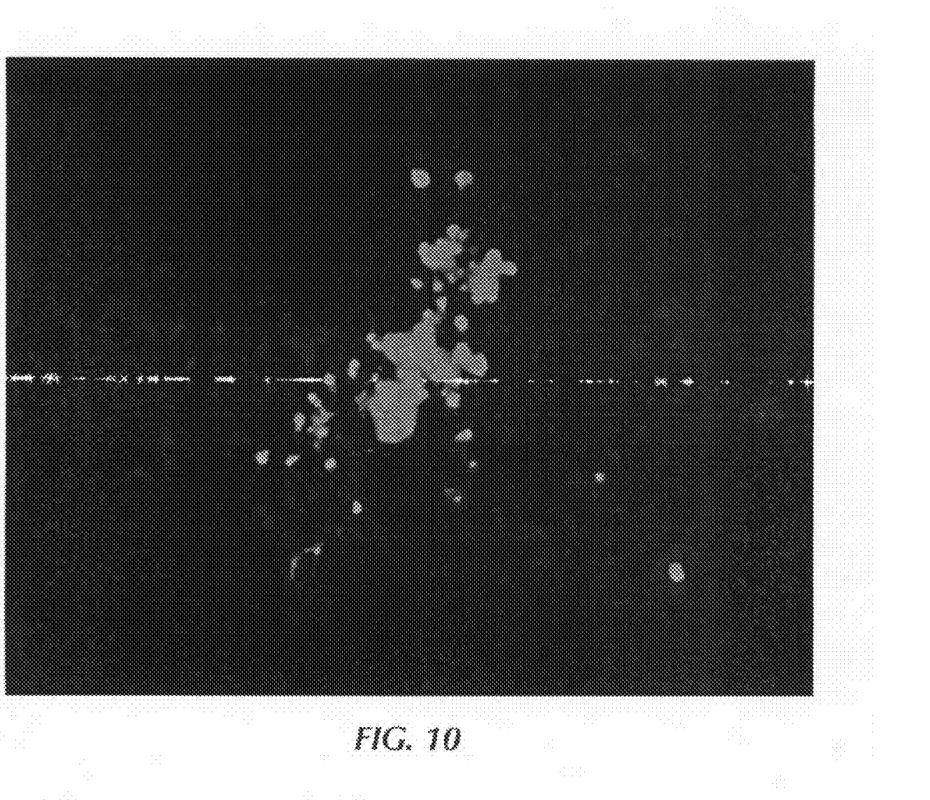
FIG. 10 is a photograph of fluorescent labeled UCB cells that were pretreated with phosphate buffered saline and then cultured for 7 days on a Fibra-Cell scaffold prepopulated with bone marrow MSCs.

FIG. 9 illustrates a representative field (200×) of the Diprotin A treated UCB cells that had been incubated in the first RCCS vessel with MSCs cultured on Fibra-Cel scaffolds for 7 days; whereas FIG. 10 illustrates a representative field (200×) of the PBS treated UCB cells that had been incubated in the second RCCS vessel with MSCs cultured on Fibra-Cel scaffolds for 7 days. The scaffold shown in FIG. 9 that was taken from the first RCCS vessel (the Diprotin A treated cells) has many more UCB cells than the scaffold shown in FIG. 10 that was taken from the second RCCS vessel (the PBS treated cells).

Harvesting the HSCs from the Artificial Niche

In the 1970s it was observed that chemotherapy could increase circulating HSCs. In the 1980s the first transplants using peripheral blood HSCs mobilized by chemotherapeutic agents were performed (Kessinger, A., et al. "Reconstitution of human hematopoietic function with autologous cryopreserved circulating stem cells'" Exp. Hematol. 14:192-196, 1986). Currently, the standard method of mobilization of HSCs for transplantation is granulocyte colony-stimulating factor (G-CSF) (Anderlini, P., et al. "Peripheral blood stem cell donation: an analysis from the International Bone Marrow Transplant Registry (IBMTR) and European Group for Blood and Marrow Transplant (EBMT) databases", Bone Marrow Transplant 27:689-692).

Recently, much of the research on HSC mobilization has focused on small molecule regulators of specific pathways of HSC trafficking, in particular the stromal cell derived factor-1 (SDF-1/CXCL12) pathway. SDF-1 secreted by stromal cells is a potent chemoattractant for HSCs which express the receptor for SDF-1, CXCR4. The SDF-1/CXCR4 interaction plays a critical role in HSC mobilization and engraftment (Lapidot, T. and Kollet, O. "The essential roles of the chemokine SDF-1 and its receptor CXCR4 in human stem cell homing and repopulation of transplanted immune-deficient NOD/SCID and NOD/SCID/B2m(null) mice. Leukemia 16:1992-2003, 2002; Levesque, J. P., et al. "Disruption of the CSCR4/CXCL12 chemotactic interaction during hematopoietic stem cell mobilization induced by GCSF or cyclophosphamide", J. Clin. Invest. 111:187-196, 2003).

Among the best studied of the small molecule regulators is AMD3100 (plerixafor), an antagonist of SDF-1 binding to CXCR4. AMD3100 induces measurable mobilization of HSCs within 1 hour in vivo (Broxmeyer, H. E., et al. "Rapid mobilization of murine and human hematopoietic stem and progenitor cells with AMD3100, a CXCR4 antagonist", J. Exp. Med. 201:1307-1318, 2005) whereas G-CSF-induced mobilization can take several days.

Embodiments for the bioprocessing and expansion of stem cells using an artificial niche utilize various chemoattractants of HSCs such as G-CSF and AMD3100 to mobilize UCB stem cells from the artificial stem cell niche.

After 24 hours to allow UCBs to home to the artificial niche, the vessel is flushed with media via the dual valving member 110 until no labeled cells are observed in the media. Then, G-CSF (from about 10 ng/ml to about 100 ng/ml) or AMD3100 (from about 100 ng/ml to about 1000 ng/ml) (both from Sigma Aldrich) is injected into the vessel. Fluid samples from the G-CSF treated samples will be taken every 12 hours by flushing the vessel with 100 ml of media. For AMD3100 treated sample, samples will be taken from the culture chamber every hour for 6-8 hours. The UCB cells mobilized from the artificial niche will be quantitated by flow cytometry.

Immunophenotyping of UCB Cells Sequestered in the Artificial Niche and Harvested from the Artificial Niche The immunotypes of the UCB cells grown in co-cultures of HSCs and stromal cells on scaffolds cultured in the RCCS vessel will be investigated prior to and after mobilization with G-CSF and AMD3100. The UCB cells residing in the artificial niche, before the chemically stimulated mobilization of the cells, will be collected using collagenase treatment. Collagenase has been used to isolate stromal and hematopoietic stem cells from bone (Stem Cell Technologies, Technical Bulletin: A guide to solid tissue dissociation).

Fibra-Cel scaffolds with MSCs and co-cultured UCBs will be removed from the vessel and placed in a 15 ml conical centrifuge tube with 10 ml of 0.25% collagenase type I. The tube will be placed in a 37° C. shaker and agitated at 200 rpm for 45 min. The tubes will then be centrifuged and the cells resuspended in 1 ml of PBS. The cells will then be labeled with antibodies against cell surface markers CD34, Thy-1 (CD90), c-kit (CD117), and CD133 and quantitated by flow cytometry.

The UCB cells chemically mobilized from the artificial niche will be immunotyped and compared to the cells released from the artificial niche by collagenase. If the two agents, G-CSF and AMD3100, mobilize different types of cells from the artificial niche, the types of cells mobilized may provide insight into how these agents differ. After establishing the optimum dose and kinetic profile of each agent in mobilizing the UCBs from the artificial niche, the cells released from the niche will be collected from the from the vessel, centrifuged, labeled with antibodies for the specific markers and quantitated by flow cytometry.

Using the CFC assay, the cells mobilized by G-CSF or AMD3100 will be compared for their multipotential and lineage restricted hematopoietic progenitors. Mobilized cells from G-CSF or AMD3100 treatment will be harvested from the RCCS, suspended in methylcellulose-based media with growth factors and cytokines (MethoCult, Stem Cell Technologies) and plated in 35 mm Petri dishes. After incubation for 14 days at 37° C. in a humidified incubator at 5% $CO_2$ erythroid (CFU-E), granulocyte/macrophage (CFU-GM), granulocyte (CFU-G), macrophage (CFU-M) and multipotential granulocyte, erythroid, macrophage, megakaryocyte (CFUGEMM) colonies will be quantitated.

Assessing the Regenerative Capacity of the Artificial Niche after Cell Mobilization A hallmark of the bone marrow is the ability to continuously generate hematopoietic progenitors. This attribute is based on the presence of self-renewing stem cells. To be able to mimic this activity in the artificial niche is highly desirable since it is desirable to expand the number of engraftable cells from UCBs. Therefore after the initial mobilization experiments with G-CSF and AMD3100, the artificial niche will continue to be cultured over 4 to 6 weeks and at two week intervals the cell population on the scaffolds will be immunophenotyped.

Although the present invention and its advantages have been described in detail, it should be understood that various changes, substitutions and alterations can be made herein without departing from the spirit and scope of the invention as defined by the appended claims.

What is claimed is:
1. A stem cell niche having:
  (a) a plurality of stromal mesenchymal stem cells seeded on a scaffold; and
  (b) a plurality of umbilical cord blood stem cells supported by the mesenchymal stem cells cultured on the scaffold; wherein the umbilical cord blood stem cells are grown in the presence of the mesenchymal stem cells cultured on the scaffold in a rotating culture chamber having a dual flow valving member at each end of the culture chamber, wherein a first flow path passes under a molecular weight cut-off membrane covering a central core that transverses the culture chamber and a second flow path passes through the culture chamber and allows cells to be harvested while in suspension.

* * * * *